(12) United States Patent
Granfors et al.

(10) Patent No.: US 6,498,831 B2
(45) Date of Patent: Dec. 24, 2002

(54) PANEL DETECTOR PIXEL REPLACEMENT METHOD AND APPARATUS

(75) Inventors: Paul R. Granfors, Sunnyvale, CA (US); Gerhard H. Brunst, Sunnyvale, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 47 days.

(21) Appl. No.: 09/746,830

(22) Filed: Dec. 22, 2000

(65) Prior Publication Data
US 2002/0080917 A1 Jun. 27, 2002

(51) Int. Cl.$^7$ .................................................. H05G 1/64
(52) U.S. Cl. ...................... 378/98.8; 378/98.2; 378/19; 378/62; 382/275; 348/246
(58) Field of Search ............................... 378/98.8, 98.2, 378/19, 62, 98, 207; 382/254, 275, 205; 358/448; 348/296, 247, 241; 250/370.09

(56) References Cited

U.S. PATENT DOCUMENTS

| 5,805,216 | A | * | 9/1998 | Tabei et al. ................... 348/246 |
| 5,875,040 | A | * | 2/1999 | Matraszek et al. ........... 358/453 |
| 6,002,433 | A | * | 12/1999 | Watanabe et al. ............ 348/246 |
| 6,104,839 | A | * | 8/2000 | Cok et al. ..................... 382/254 |
| 6,359,967 | B1 | * | 3/2002 | Bielski et al. ............... 378/98.2 |

* cited by examiner

Primary Examiner—Drew A. Dunn
(74) Attorney, Agent, or Firm—Fletcher, Yoder & Van Someren

(57) ABSTRACT

A technique for generating replacement values for defective pixels in a digital imaging system includes generating a base values for the defective pixels and a statistical characterizing values which provide consistent statistical relationships with other pixels. The base values may be computed as mean values of pixels surrounding the defective pixels. The statistical characterizing values may be selected to provide deviation from the mean values by a standard deviation of other selected pixels, such as pixels in the neighborhoods of the defective pixels. The technique avoids image artifacts due to inconsistent noise or other statistical characteristics in the pixel replacement values.

33 Claims, 3 Drawing Sheets

PANEL DETECTOR PIXEL REPLACEMENT METHOD AND APPARATUS

FIELD OF THE INVENTION

The present invention relates generally to discrete pixel detectors, such as those used in digital x-ray imaging systems. More particularly, the invention relates to a technique for replacement of information for defective pixels in a panel to provide useful image data for processing and reconstruction.

BACKGROUND OF THE INVENTION

Discrete pixel imaging systems, such as digital x-ray imaging systems, are becoming increasingly widespread for producing digital data which can be reconstructed into useful images. In current digital x-ray imaging systems, radiation from a source is directed toward a subject, typically a patient in a medical diagnostic application. A portion of the radiation passes through the patient and impacts a detector. The surface of the detector converts the radiation to light photons which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

Digital x-ray imaging systems are particularly useful due to their ability to collect digital data which can be reconstructed into the images required by radiologists and diagnosing physicians, and stored digitally or archived until needed. In conventional film-based radiography techniques, actual films were prepared, exposed, developed and stored for use by the radiologist. While the films provide an excellent diagnostic tool, particularly due to their ability to capture significant anatomical detail, they are inherently difficult to transmit between locations, such as from an imaging facility or department to various physician locations. The digital data produced by direct digital x-ray systems, on the other hand, can be processed and enhanced, stored, transmitted via networks, and used to reconstruct images which can be displayed on monitors and other soft copy displays at any desired location.

In discrete pixel imaging detectors, such as those used in digital x-ray systems, it is not uncommon for detector output levels to vary between pixels, even when the pixels are exposed to equal levels of radiation. Such variations may be due to tolerances within the sensitivity of the detector itself, as well as to various forms of noise which may occur in the detection system. Similar differences may originate in the normal variations in the structures and performance of the circuitry associated with the individual pixels. However, while certain normal variations may be permitted, significant differences in pixel-to-pixel output from the detector are not desirable.

Such pixel-to-pixel output variations may involve both underactive pixels (i.e., those regions producing a signal significantly lower than other regions for the same received radiation) and overactive pixels (i.e., regions producing output levels significantly higher than other regions for the same received radiation). In addition to producing erroneous dark or light artifacts in the resulting image, data from such underactive or overactive pixels can adversely affect signal processing operations performed on the image, such as adjustment of contrast and tone, as well as errors in dynamic range detection and image enhancement.

Defects in pixels in solid state detectors may result from various causes. For example, high leakage currents, open circuits and short circuits can cause pixels erroneously to output signals when no significant radiation levels have impacted their locations, or to output abnormally low signal levels when radiation has impacted the pixels. It would be useful, therefore, to identify potentially defective detector pixels so as to avoid erroneous data in discrete pixel images produced from the detector output. Where significant output differences are detected between pixels of a detector, it may be useful to flag such pixels as defective, and to manage information they provide in a special manner, or simply to disregard their output.

Various approaches have been proposed for handling information voids left by defective pixels in such situations. For example, rather than simply omitting information at the defective pixel locations in the reconstructed image, certain processing techniques provide for filling the information voids with an average value of neighboring pixels. However, such techniques do not preserve the statistical integrity (e.g. characterizing noise) of the image data, and may therefore skew analyses performed on the data, such as for subsequent filtering and image processing and enhancement.

There is a need, therefore, for an improved technique for addressing information voids caused by defective pixels or aberrant pixel values in digital imaging systems. There is a particular need for a system which would allow useful images to be produced without altering the overall statistical characteristics of the image data.

SUMMARY OF THE INVENTION

The present technique provides a novel approach to pixel value substitution designed to respond to such needs. The technique may be employed in new systems or software packages configured to process digital image data, and may also be retrofitted to existing systems to enhance image quality. The approach provides values for missing or aberrant data, such as might result from one or more defective pixel circuits in a detector or detector data processing modules. The technique is particularly well suited to digital x-ray imaging systems, but may be applied in a wide range of fields where aberrant pixel data can be recognized and where replacement values may be useful in providing a more meaningful set of image data.

The technique preserves the statistical nature of the image data while offering the replacement values desired for defective pixels. In general, a base value for missing or aberrant pixel data is computed, such as by reference to other pixels in a row, column or neighborhood. Statistical characteristics of the image data are computed, such as a standard deviation value. The statistical characteristics may be reflective of noise in the image data or in a portion of the image data. A value preserving the statistical characteristics is used to complement the base value, thereby preserving the characteristics in the replacement value.

DETAILED DESCRIPTION OF THE INVENTION

Figure 1:
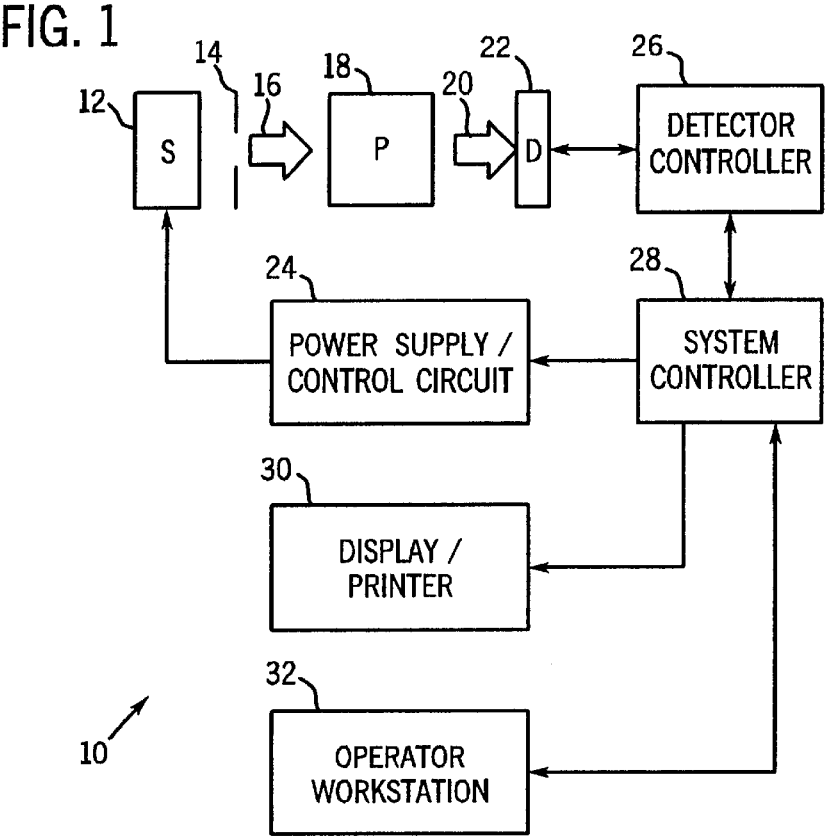
FIG. 1 is a diagrammatical overview of a digital x-ray imaging system in which the present technique is incorporated.

FIG. 1 illustrates diagrammatically an imaging system 10 for acquiring and processing discrete pixel image data. In the illustrated embodiment, system 10 is a digital x-ray system designed both to acquire original image data, and to process the image data for display in accordance with the present technique. In the embodiment illustrated in FIG. 1, imaging system 10 includes a source of x-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital x-ray detector, represented generally at reference numeral 22. As described more fully below, detector 22 converts the x-ray photons received on its surface to lower energy photons, and subsequently to electric signals which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
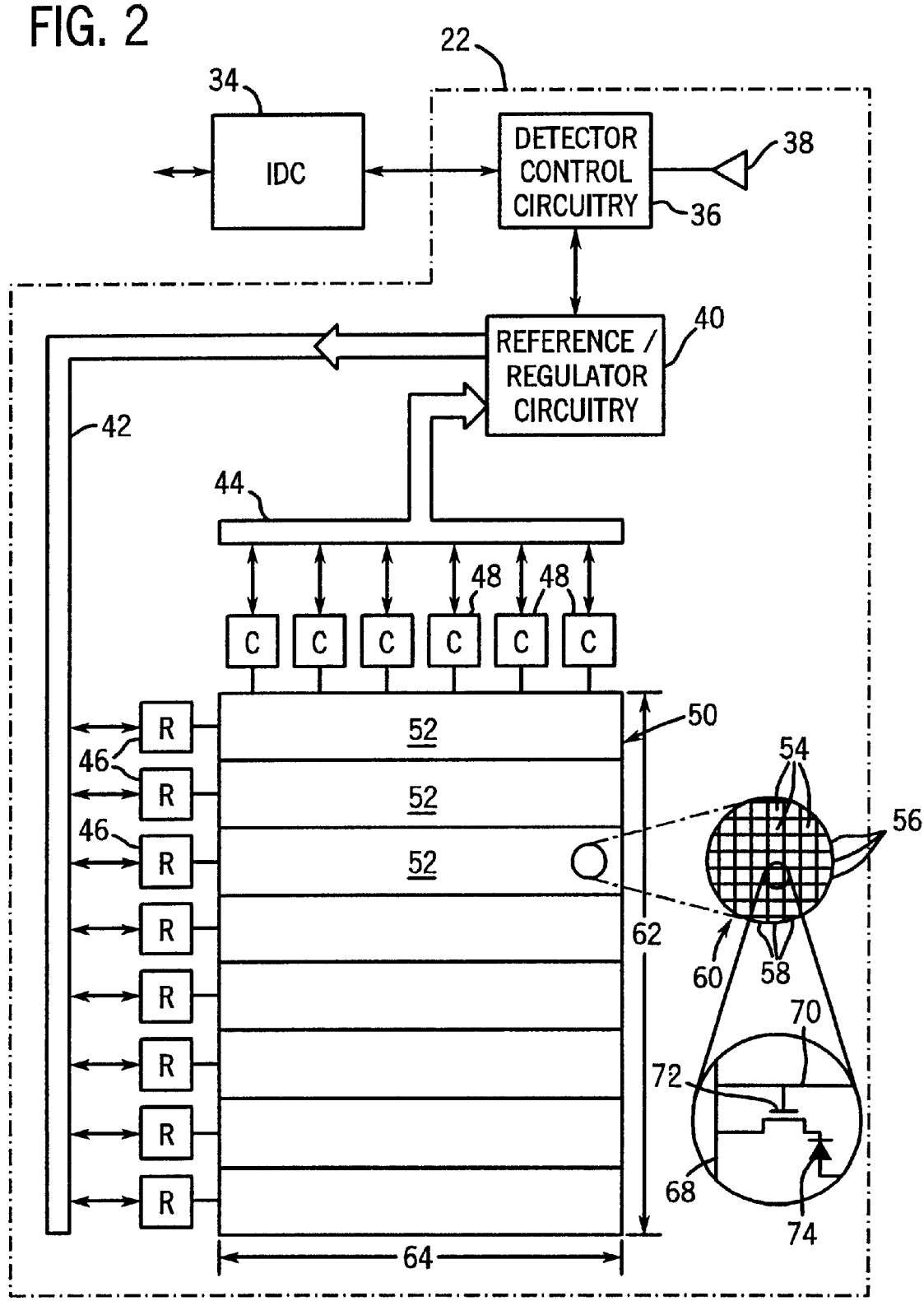
FIG. 2 is a diagrammatical representation of certain of exemplary functional circuitry for producing image data in a detector of the system of FIG. 1 to produce image data for reconstruction.

FIG. 2 is a diagrammatical representation of functional components of digital detector 22. FIG. 2 also represents an imaging detector controller or DC 34 which will typically be configured within detector controller 26. DC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a presently preferred embodiment illustrated, detector 22 consists of a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photodetectors is formed of amorphous silicon deposited on a glass substrate. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
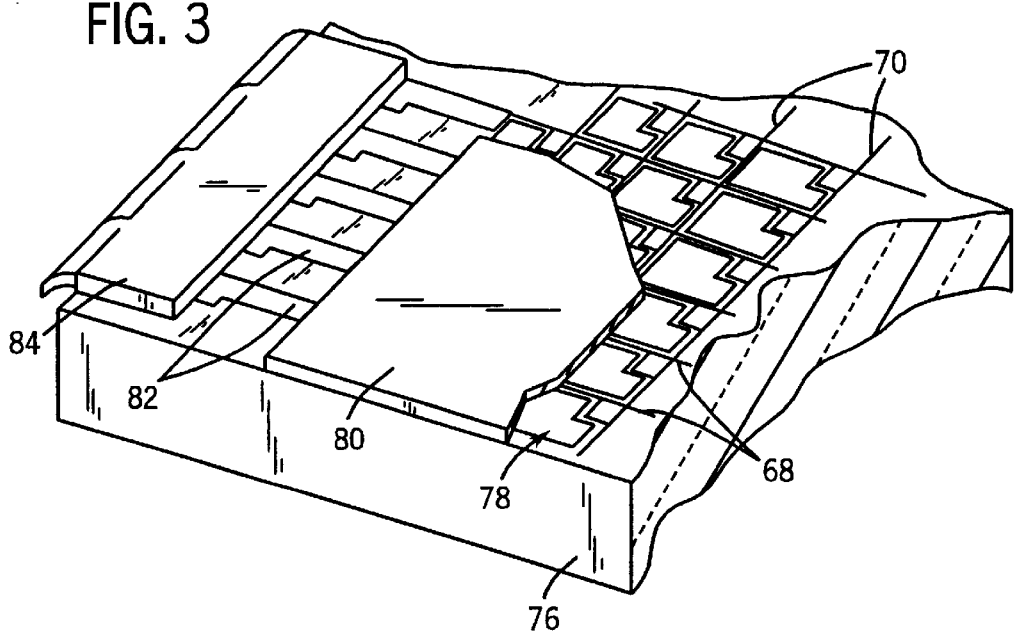
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

In digital imaging systems, such as the x-ray system described above, information collected at certain pixel locations may prove to be aberrant or defective. For example, the circuitry used to sense the photons received by the detector may be defective after initial manufacture, or may become defective over time, producing either values which are inconsistently high or values which are inconsistently low as compared to other values in the image matrix. A number of approaches have been proposed and are currently available for identifying such defective pixels. For example, configuration or calibration exposures may be made, wherein a known radiation level is directed to the detector, and pixel values are readout. In single or multiple exposures, and with reference to various exposure levels, pixels which provide output values beyond statistical limits may be tagged as defective. In certain cases, such pixels will be isolated in the image matrix, or may be grouped in a specific location or along a specific row or column. The present technique is employed to provide replacement values for those pixels which have been identified as producing aberrant values.

Figure 4:
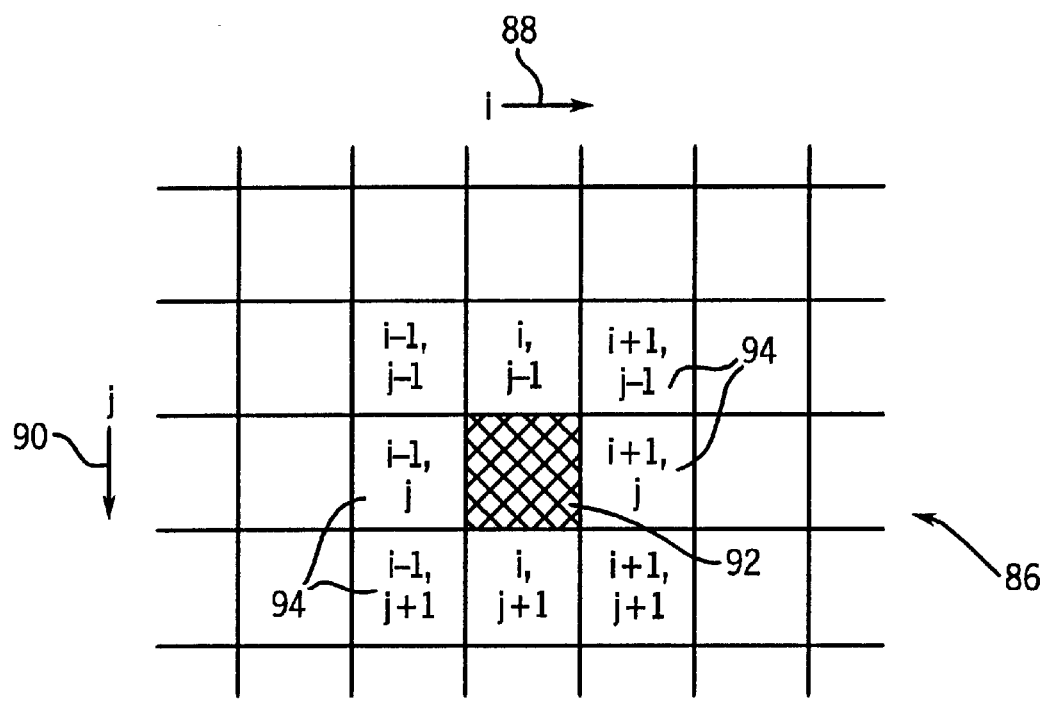
FIG. 4 is a more detailed view of a portion of an image matrix of the type used to generate and reconstruct images in a system of the type shown in the preceding Figures, with a defective pixel location indicated as surrounded by neighboring pixels.

FIG. 4 illustrates a portion of an image matrix, such as that described above with respect to the implementation in a digital x-ray system. As illustrated in FIG. 4, a pixel neighborhood 86 comprises a portion of the image matrix, and extends over a series of rows 88 and columns 90. In the illustration of FIG. 4, the individual rows, extending generally parallel to the arrow 88, are designated based upon their relationship to a base i, while the columns, extending parallel to columns 90, are denoted by their relationship to a base location j. A defective pixel 92 is located at a center of the neighborhood 86, at a location which would correspond to coordinates (i, j). Again, the defective pixel 92 may, in fact, contain defective data-producing circuitry, or may be coupled to circuitry, such as for readout, which is defective. In any event, however, the pixel is identified as producing aberrant data for which a replacement value is desired.

Within neighborhood 86, defective pixel 92 is surrounded by neighboring pixels 94. In the notation indicated in FIG. 4, the pixels may be identified by their location with respect to the coordinates of the bad pixel, that is, (i, j). It should be noted that, in the example illustrated in FIG. 4, a single bad pixel 92 is identified. However, in certain situations, a series of pixels forming a localized group, or extending along a particular row or column of the detector may be identified as defective. In the case of bad rows or columns, defects in the pixels may, in fact, be tied to defects in the readout or enabling circuitry used to link the pixel circuitry to the readout and data processing components described above.

While heretofore known techniques have been provided for replacement of a value for a pixel such as pixel 92 in FIG. 4, these techniques have typically relied upon simple averaging of neighboring pixels, such as pixels of a row (i−1, j) and (i+1, j) surrounding the pixel 92 in FIG. 4. Similar approaches may average values along a row, such as by reference to pixels (i, j−1) and (i, j+1) in FIG. 4. However, it has been found that such approaches do not preserve the statistical characteristics of the overall image data. Specifically, subsequent image processing, such as filtering, structure identification, image enhancement, and so forth, may be skewed or rendered inaccurate or less than optimal by the absence of similar statistical properties in the pixel replacement values. Other approaches, such as interpolation between surrounding pixels, suffer from similar drawbacks. These drawbacks may ultimately result in artifacts in the final reconstructed image. It has been found that for example, where the statistical characteristics of the replacement value is not preserved, a flat field image containing such replacement values will have a noise component that is smaller than that of surrounding pixels, such as by a factor of the square root of two where the replacement value is based upon an average of two pixels. Such artifacts can be noticeable both in still images and when viewing the images in a sequence. Again, such artifacts also adversely effect the quantitative analysis performed on the image data.

The present technique has been developed to reduce the incidents of such artifacts and to improve overall quality. It has been found that by adding a random value to the pixel replacement base value, the statistical characteristics of the image data can be maintained. Specifically, in a present implementation, a random value has a mean of zero and a standard deviation which will make the statistical characteristic of the replacement pixel value the same as that of its neighbors, or of a defined neighborhood or portion of the image, or of the entire image.

By way of example, when replacing a pixel value along a column such as that illustrated in FIG. 4, where the desired replacement value is indicated by the variable image (i, j), the replacement value may be determined by the relationship:

$$\text{image}(i, j) = 0.5(\text{image}(i, j-1) + \text{image}(i, j+1)) + RN,$$

where the values image (i, j−1) and (image)j+1 are the values of neighboring non-defective pixels, and RN is a random number with a mean of zero and a standard deviation equal to the standard deviation of the surrounding pixel values divided by the square root of two.

It should be noted that this particular embodiment utilizes neighboring pixels along the ith column as the basis for determining an average value, complimented by the value RN to conform the replacement base value to the statistical characteristics of the image data. However, other neighborhoods may be used in the computation, including neighborhoods of neighboring pixel values in rows, or neighboring pixel values within expanded row and column neighborhoods, such as the 3×3 neighborhood illustrated in FIG. 4. It should also be noted, that the value RN is generated based upon the standard deviation of any relevant portion of the image, such as the standard deviation in a 3×3 neighborhood of the type illustrated in FIG. 4. Alternatively, standard deviations within a selected section of the image, or within the entire image may be utilized for generation of the statistical characterizing component of the replacement value. Still further, where analyses are performed on the image data, a standard deviation value derived from such analyses may be employed, such as a standard deviation value for structural features, background features, and so forth. Finally, the division by the square root of two in the foregoing discussion for generation of the value RN is based upon the use of two values to generate the base value for the replacement. Where more than two pixel values are used in the calculation, a corresponding square root of that integer number is used.

Other reference values may be used for generating the replacment value, where desired. Indeed, many acceptable approached may be used for deriving the statistical characterizing component of the replacement value. For example, rather than by reference to the statistical characteristics of other pixels in a single image, values for pixels across a series of images may be used to determine statistical characteristics of noise for use in determing the value RN. Similarly, values for the same pixel (which may, for example, intermittently generate aberrant values, may be used to determine the statistical characterizing value. Finally, the statistical characterizing value used with the base value may be based upon knowledge of anticipated or expected noise for the same or other pixels from calibration or knowledge database, such as by reference to the calculated base value (e.g. implemented by a lookup table or a similar approach).

Figure 5:
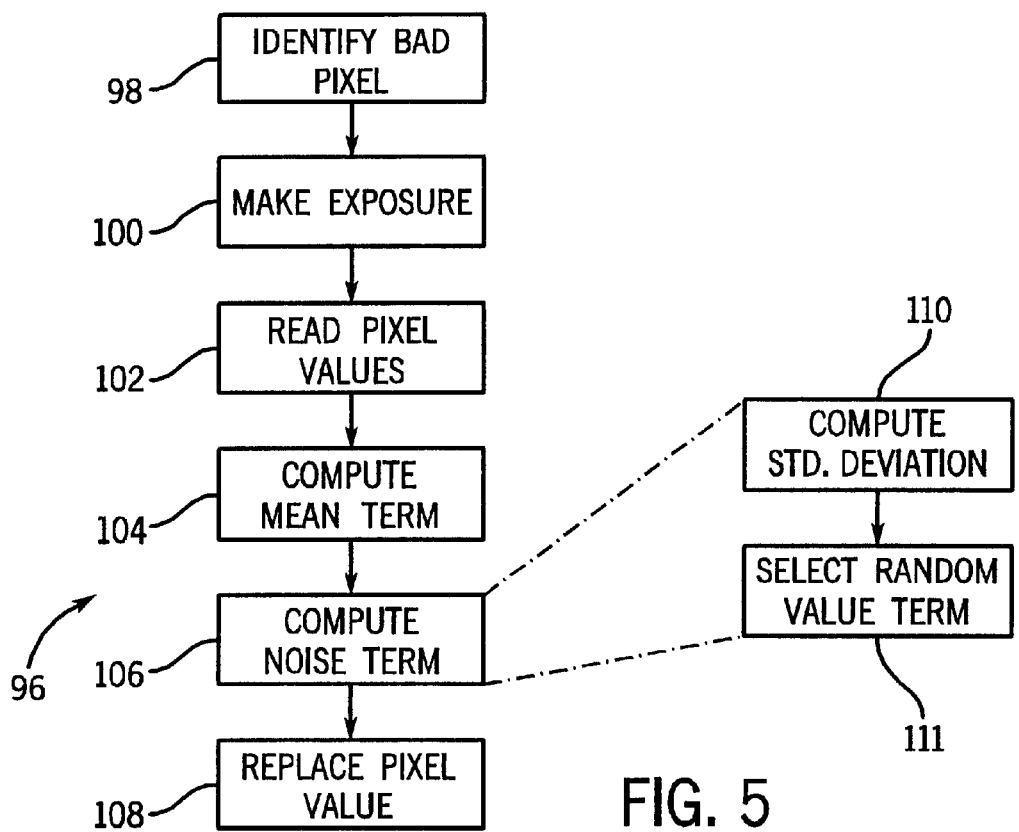
FIG. 5 is a flow chart illustrating exemplary control logic for generating a replacement value for aberrant or defective pixel data.

The foregoing approach to generating defective pixel replacement values is summarized in the flow chart of FIG. 5. The procedural logic, identified by reference numeral 96, begins with identification of the aberrant or bad pixels as indicated at step 98. As noted above, this identification may proceed in any suitable manner, such as by analysis of values sampled from the pixels in calibration or test sequences or exposures. Once the aberrant pixel locations are identified, a conventional exposure is made as indicated at step 100. The values for the pixels resulting from the exposure are collected at step 102 as set forth above.

Preferably prior to image enhancement and filtering techniques, the replacement values for any aberrant pixels are computed. Thus, in FIG. 5, at step 104 the base or mean term of the relationship described above is calculated based upon the desired neighborhood. It should be noted that the particular values used to compute the mean value may be a function of the pattern in which the aberrant pixel or pixels appear. For example, where an entire row is determined to be defective, the mean terms for the pixels of the row may be more appropriately identified by reference to neighboring rows or an expanded neighborhood. Next, at step 106, the "noise" or statistical characterizing term corresponding to the term RN used to modify the base value to accommodate the statistical characteristics of the image data is computed. Based upon the resulting mean term and the noise term, the replacement pixel value is generated at step 108. Subsequent processing may proceed in otherwise conventional manners.

As noted above, computation of the noise term at step 106 may include a series of sub-routines, including the computation of a standard deviation value at step 110, and a selection of a random value term at step 111. As noted above, the standard deviation term computed at step 110 may be based upon a local pixel neighborhood, an expanded neighborhood, or any desired logical subdivision of the image data. Moreover, selection of the random value term at step 111 is performed to provide a zero mean for the value RN, with the same standard deviation as that computed at step 110.

Also as noted above, the statistical characterizing value may be derived from values of other pixels in a series of images, same pixel in a series of images, knowledge of anticipated or expected noise for the same or other pixels from calibration or knowledge database, such as by reference to the calculated base value.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating replacement pixel values in a digital imaging system, the method comprising the steps of:
   generating a base value for a desired pixel;
   generating a statistical characterizing value for the desired pixel; and
   combining the base value and the statistical characterizing value to obtain a replacement pixel value.

2. The method of claim 1, wherein the base value is generated based upon values for pixels neighboring the desired pixel in a row of an image matrix.

3. The method of claim 1, wherein the base value is generated based upon values for pixels neighboring the desired pixel in a column of an image matrix.

4. The method of claim 1, wherein the base value is generated based upon values for pixels neighboring the desired pixel in surrounding rows and columns of an image matrix.

5. The method of claim 1, wherein the statistical characterizing value is generated to maintain consistent statistical characteristics between the desired pixel and neighboring pixels in an image matrix.

6. The method of claim 5, wherein the statistical characteristics include mean and standard deviation values.

7. The method of claim 6, wherein the statistical characterizing value is generated to maintain a mean of zero and a standard deviation equal to a standard deviation of a selected group of pixels in an image matrix.

8. The method of claim 1, wherein the statistical characterizing value is selected to maintain a consistent level of noise in the replacement pixel value as compared to a selected group of pixels in an image matrix.

9. A method for generating replacement values for defective pixels in a digital detector, the rmethod comprising the step of:
   collecting an image data set for rows and columns of pixels of a detector, the detector including at least one pixel identified as defective;
   computing a base value for the defective pixel based upon values of neighboring pixels in the image data set;
   computing statistical data for the image data set; and
   computing a replacement value for the defective pixel based upon a combination of the base value and the statistical data.

10. The method of claim 9, comprising the step of processing the image data set including the replacement value for the defective pixel.

11. The method of claim 9, wherein the base value is a mean of values of pixels neighboring the defective pixel.

12. The method of claim 11, wherein the base value is a mean of values of pixels neighboring the defective pixel in a row.

13. The method of claim 11, wherein the base value is a mean of values of pixels neighboring the defective pixel in a column.

14. The method of claim 11, wherein the base value is a mean of values of pixels neighboring the defective pixel in at least one row and at least one column.

15. The method of claim 9, wherein the statistical data includes standard deviation data for at least a neighborhood of pixels around the defective pixel.

16. The method of claim 9, wherein the replacement value is computed to maintain a consistent level of noise in the neighborhood of the defective pixel.

17. The method of claim 9, wherein the replacement value is computed to provide deviation from the base value having a statistical mean of zero and a standard deviation equal to a standard deviation value for pixels neighboring the defective pixel.

18. A method for generating replacement values for defective pixels in a digital detector, the method comprising the step of:

accessing an image data set for rows and columns of pixels of a detector, the detector including at least one pixel identified as defective;

computing a base value for the defective pixel that is a mean of values of neighboring pixels in the image data set;

computing a characterizing value for the defective pixel, the characterizing value being selected to provide a desired deviation from the base value having a mean of zero and a standard deviation equal to a standard deviation value for a desired set of pixels in the image data set; and computing a replacement value for the defective pixel based upon the base value and the characterizing value.

19. The method of claim 18, wherein the neighboring pixels include pixels adjacent to the defective pixel in a row.

20. The method of claim 18, wherein the neighboring pixels include pixels adjacent to the defective pixel in a column.

21. The method of claim 18, wherein the neighboring pixels include pixels adjacent to the defective pixel in at least one row and at least one column.

22. The method of claim 18, wherein the desired set of pixels includes pixels adjacent to the defective pixel in a row.

23. The method of claim 18, wherein the desired set of pixels includes pixels adjacent to the defective pixel in a column.

24. The method of claim 18, wherein the desired set of pixels includes pixels surrounding the defective pixel in at least one row and at least one column.

25. A digital imaging system comprising:

a detector having an image matrix of rows and columns of pixels, the image matrix including a pixel designated as defective; and signal processing circuitry coupled to the detector and configured to sample pixel values from the detector and to compute a replacement value for the defective pixel by computing a base value and combining the base value with a computed statistical characterizing value, the statistical character value providing a consistent statistical relationship between the replacement value and values for pixels at least in a neighborhood of the defective pixel.

26. The system of claim 25, comprising an x-ray source, and wherein the detector samples the pixel values resulting from exposure to an x-ray beam from the x-ray source.

27. The system of claim 25, wherein the base value is computed as a mean of values of pixels in the neighborhood of the defective pixel.

28. The system of claim 25, wherein the statistical characterizing value maintains a consistent level of noise between the replacement value and values for pixels at least in a neighborhood of the defective pixel.

29. The system of claim 25, wherein the statistical relationship includes a standard deviation value.

30. A digital x-ray system comprising:

an x-ray source;

a detector for generating pixel values in response to exposure to an x-ray beam from the source, the detector having an image matrix of rows and columns of pixels, the image matrix including a pixel designated as defective;

signal processing circuitry coupled to the detector and configured to sample the pixel values from the detector and to compute a replacement value for the defective pixel by computing a base value and combining the base value with a computed statistical characterizing value, te statistical characterize value providing a consistent statistical relationship between the replacement value and values for pixels at least in a neighborhood of the defective pixel.

31. The system of claim 30, wherein the base value is computed as a mean of values of pixels in the neighborhood of the defective pixel.

32. The system of claim 30, wherein the statistical characterizing value maintains a consistent level of noise between the replacement value and values for pixels at least in a neighborhood of the defective pixel.

33. The system of claim 30, wherein the statistical relationship includes a standard deviation value.

* * * * *